United States Patent [19]
Brown

[11] Patent Number: 5,312,408
[45] Date of Patent: May 17, 1994

[54] APPARATUS AND MEHTOD OF CUTTING AND SUCTIONING THE MEDULLARY CANAL OF LONG BONES PRIOR TO INSERTION OF AN ENDOPROSTHESIS

[76] Inventor: Byron L. Brown, 2315 Hendricks, Fort Smith, Ark. 72903

[21] Appl. No.: 964,493

[22] Filed: Oct. 21, 1992

[51] Int. Cl.⁵ .................. A61B 17/00; A61F 2/32
[52] U.S. Cl. ........................ 606/80; 606/96; 604/119; 408/58; 408/72 R; 408/201
[58] Field of Search .............. 606/79, 80, 96, 98, 606/180; 604/116, 118, 119; 408/58, 72 R, 72 B, 115 R, 115 B, 204, 201; 623/22, 23

[56] References Cited

U.S. PATENT DOCUMENTS

| | | | |
|---|---|---|---|
| 3,694,099 | 9/1972 | Nicholas | 408/58 |
| 4,069,824 | 1/1978 | Weinstock | 408/204 |
| 4,580,414 | 5/1986 | Yoshida et al. | 606/79 |
| 4,782,833 | 11/1988 | Einhorn et al. | 606/80 |
| 4,844,064 | 7/1989 | Thimsen et al. | 606/80 |
| 4,911,253 | 3/1990 | Cliche | 408/58 |
| 4,988,336 | 1/1991 | Kohn | 604/119 |
| 5,052,411 | 10/1991 | Schoolman | 606/80 |
| 5,100,408 | 3/1992 | Lackey | 606/79 |
| 5,171,244 | 12/1992 | Laspari et al. | 606/80 |

*Primary Examiner*—John G. Weiss

[57] ABSTRACT

An apparatus and method for cutting and suctioning the medullary canal of long bones prior to insertion of an endoprosthesis. A cutter is aligned with the medullary canal and the canal is enlarged. Successively larger cutters are used in conjunction with a guide to center each cutter in the medullary canal. A suction is applied to removed bone cutting and other debris resulting from the procedure.

20 Claims, 5 Drawing Sheets

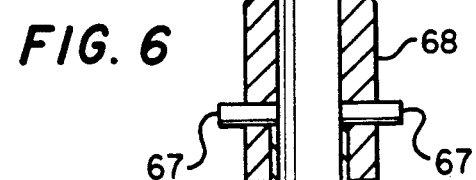
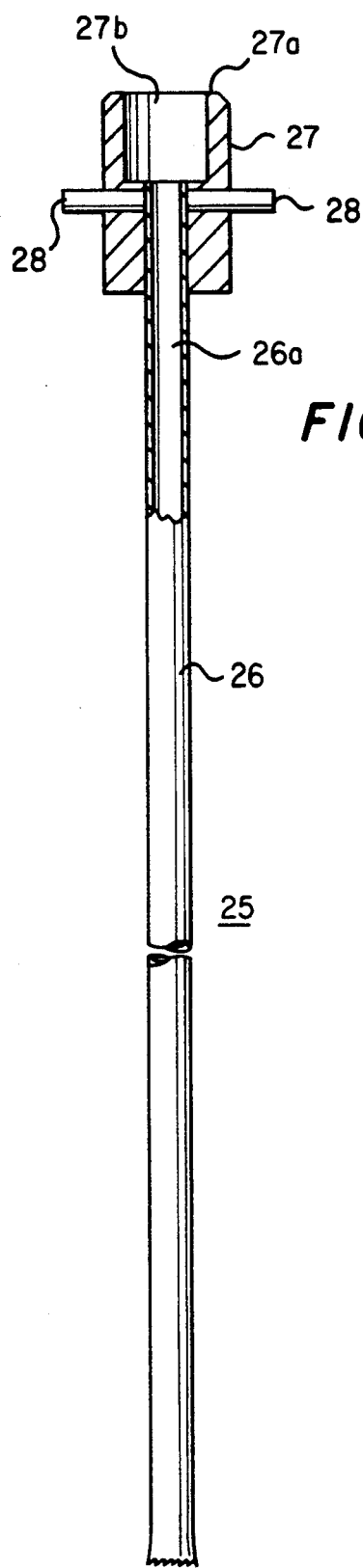
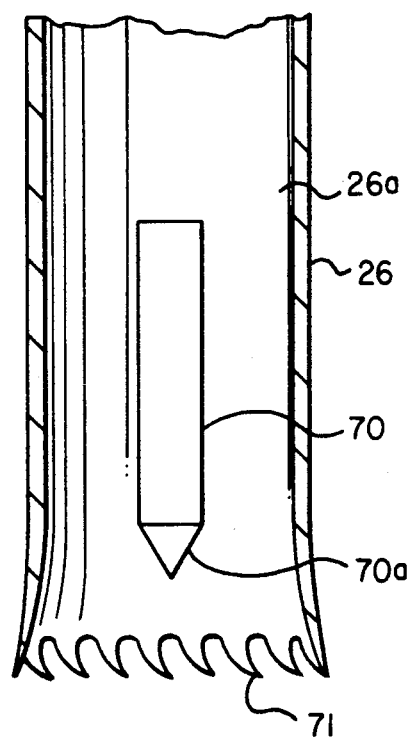

APPARATUS AND MEHTOD OF CUTTING AND SUCTIONING THE MEDULLARY CANAL OF LONG BONES PRIOR TO INSERTION OF AN ENDOPROSTHESIS

This invention relates to an apparatus and method for use in practicing orthopedic surgery and more particularly to an apparatus and method for cutting and suctioning the medullary canal of long bones prior to insertion of an endoprosthesis.

BACKGROUND OF THE INVENTION

As is known to those skilled in the art of orthopedics, the practice of orthopedic surgery often includes bone modification including cutting, suctioning and the installation of a variety of prostheses. Attendant to the practice of such procedures has been the certain side effects which are potentially injurious to a patient's health. Thus, it has been known prior to the use of endoprosthesis or intramedullary devices that fat emboli are undesirably associated with fractures of long bones. The occasional mortality with endoprosthesis and cement fixation has been considered to be primarily due to pre-operative cardiac or pulmonary diseases of the patient. However, more recently, by comparison in recent years of cemented versus non-cemented components, the increased morbidity and mortality of patients with cemented endoprostheses was considered to be due probably to the use of cemented endoprostheses in patients with greater cardiac and pulmonary and other debilitating diseases and decreased mobile capabilities. The commonly observed decrease in blood pressure was considered to be primarily a result of small amount of the monomer Methylmerthacrylate being introduced into the patient's general circulation. The drop in blood pressure was believed to be effectively controlled by reducing the depth of anesthesia shortly prior to and during the insertion oft he bone cement into the canal or cavity.

With recent employment and refinement of various imaging devices and improved method of study, recognizable changes within the vascular system at various stages of endoprosthesis surgery have been shown. Multiple unidentified particles of material generally referred to as debris are now observed and timely associated with manipulation of fractures, reaming and/or rasping of medullary bone, insertion of the endoprosthesis with or without bone cement, and performing the necessary manipulations to position the prosthetic femoral head into the acetabular area.

The observation that an increased and appreciable number of debris particles reached the right ventricle of the heart at the corresponding moment of reducing the femoral head into the acetabulum is evidence that such particles have been residing in an unidentified area and are probably moved by either elevating the leg which is necessary for reducing the head into the acetabular area and/or by stretching the muscles of the area and so the debris particles are squeezed and moved into the general circulation. If the particles are considerable in number, the patient has a slow post-operative recovery period with moderate morbidity. If the patient, preoperatively, is a poor surgical risk, the morbidity may be tremendous, and to such a degree that the patient succumbs. It is therefore desirable to decrease the number of small debris particles including fat and thereby decrease the number of emboli; to remove debris at the earliest possible moment; remove most of the fat as soon as the membrane of the fat cell is broken; remove the small debris particles as soon as the cutter has created any bone-dust and other small particles; and desirable to more effectively remove or recover the remaining debris particles which are residing in or near the operative field. Furthermore, it seems proper to avoid performing surgery which involves large medullary displacement, or removal in two long bones of a patient in the same day.

Currently, in the preparation of a long bone for receiving an endoprosthesis, such as the femoral stem, some of the medullary bone and its marrow are removed to provide space for the endoprosthesis. The bone and marrow are cut by reamers and removed by suction, irrigation and brushing. By the process of cutting there are produced multiple pieces of bone which range in size from exceedingly small pieces of hydoxyapetite to easily seen and palpable sizes. The marrow in the elderly is usually yellow marrow and consists mainly of fat cells, but in the more elderly or emaciated person, the marrow may have lost most of its fat and is identified as gelatinous marrow because of its consistency and appears somewhat reddish in color. In the epiphyseal region of long bone, there may still exist red marrow with blood forming capabilities.

Generally speaking, the removal of medullary bone and marrow, the fitting and insertion of the endoprosthesis, and the cementing of the endoprosthesis in the canal, produces debris which may consist of many different things such as clumps of blood cells, clumps of endothelial cells or bits of pieces of fibrin from vessels and cell walls, fat, pieces of bone or hydroxyapatite, and bits of Methylmerthacrylate mixed with any of the other debris, or bits of poorly polymerized or incomplete polymerization of Methylmerthacrylate.

Currently, the portion of medullary bone which is to be removed is broken up and cut up by reamers which have a cutting edge at the advancing end of the shaft and spiral grooves up the periphery of the shaft of the reamer. A reamer is therefore quite similar to a drill bit. For easy operation and speed, the reamer is often power driven. The reamers are usually used in sequence of increasing size of their cross-section diameter, thereby attempting to avoid overloading the spiral grooves with debris. However, such a system and method is accompanied by displacing some small sized particles of solid or semi-solid debris distally of further down the medullary canal, and some are moved outward to the surrounding intertrabecular spaces of the medullary bone. Broken fat cells permit the fat to be easily displaced, distally and outwardly. Some of the debris which remains in the canal, as each reamer is changed or removed, is withdrawn by suction. When the medullary canal has been reamed by the largest selected sized reamer, the canal is irrigated and suctioned and brushed repeatedly in an effort to recover the debris that rests in the intertrabecular spaces. However, some of the debris has been moved too far distally and outwardly to be recovered by brushing, irrigating and ordinary suction.

BRIEF SUMMARY OF THE INVENTION

In accordance with the present invention, an instrument is employed which can cut a central cylindrical core, and which will cut and crush into small pieces much of the medullary bone which is to be removed. The use of the cutter is combined with constant suction during the time of cutting, thus preventing the displacement of debris distally down the canal, and outwardly into the intertrabecular spaces. Furthermore, the beveling of the cutting teeth on the inside of the cylinder rather than on the outside of the cylinder helps prevent the small bits of debris from escaping to the intertrabecular spaces. The removal of debris through the cylinder prevents escape of debris into the adjacent intertrabecular spaces as currently occurs with peripheral grooves of the reamer. Removal of debris by suction through the cylinder of the cutter provides almost instantaneous removal of fat and debris from the patient In patients with a fracture of a long bone, there will already have been mobilized fat from the area, and a variable amount of fat will already have entered the general circulation. It is believed that some of such mobilized fat may not yet have reached the general circulation, but will be residing in peripheral intertrabecular spaces, and in and about the periosteum and endosteum of the bone and traumatized vessels Some of that debris can be removed by applying sustained negative pressure or suction along with periodic irrigation to the canal. The cut surface of the intertrochanteric area of the femur may be closed or sealed by employing definitive cutters as described in my co-pending U.S. patent application Ser. No. 07/850,846 (filed Mar. 13, 1992), by perfecting the seal with a small amount of bone cement on the cut surface of the cortex, and by applying a ceiling to the cemented and cut surface of the femur after the base-guide has been pinned to the proximal femur. The seal is accomplished by a gasket-like piece of silicone rubber properly positioned between the ceiling and cemented surface of the femur, and by the ceiling being tightly secured to the base-guide. Irrigation of the canal can be accomplished by injecting irrigating fluid through an inlet valve in the ceiling and an opening in the ceiling and gasket to the medullary cavity.

Suctioning can be accomplished with a suction tube attached to a suction head attached to the cutter, and mounted between the cutter and the rotary power source that turns the cutter. The suction path is through the center of the cutter into the suction head. A vacuum is drawn through the suction head and the cutter to removed cutting debris.

For the ceiling of the suction assembly, it is desirable to have a one piece ceiling which matches the ceiling of the pressure assembly, and glue the entire sealer to the underside of the ceiling.

By providing a one piece ceiling with a ceiling fixed to the underside of the ceiling and inserting the gasket, the suction assembly is easily secured to the base-guide by four bolts which pass through the walls of the ceiling and into the base-guide, although the suction assembly could be held in place manually by using a thick ceiling. Furthermore, the pressure assembly is thereby available to the scrub nurse for removal of the trial stem and insertion of the definitive stem while the surgeon removes the proper amount of medullary bone and debris from the canal with the cutters and suction assembly.

Along with the suction assembly, it is desirable to record the amount of negative pressure, and such is provided by a gauge which records positive and negative pressure. To avoid interference with the cylinders of the suction cutters, an adaptor may be used which arises from the ceiling a short distance and then extends at a right angle to avoid collision with the cutter cylinders. It is desirable to measure negative pressure since excessive negative pressure can cause excess bleeding into the bond canal.

The technical advance represented by the invention, as well as the objects thereof, will become apparent from the following description of a preferred embodiment of the invention when considered in conjunction with the accompanying drawings, and the novel features set forth in the appended claims.

BRIEF DESCRIPTION OF THE DRAWINGS

FIG. 5 illustrates a small diameter cutter;

FIG. 5a illustrates the tooth end of a cutter;

FIG. 6 illustrates a large diameter cutter;

DESCRIPTION OF A PREFERRED EMBODIMENT

Figure 1:
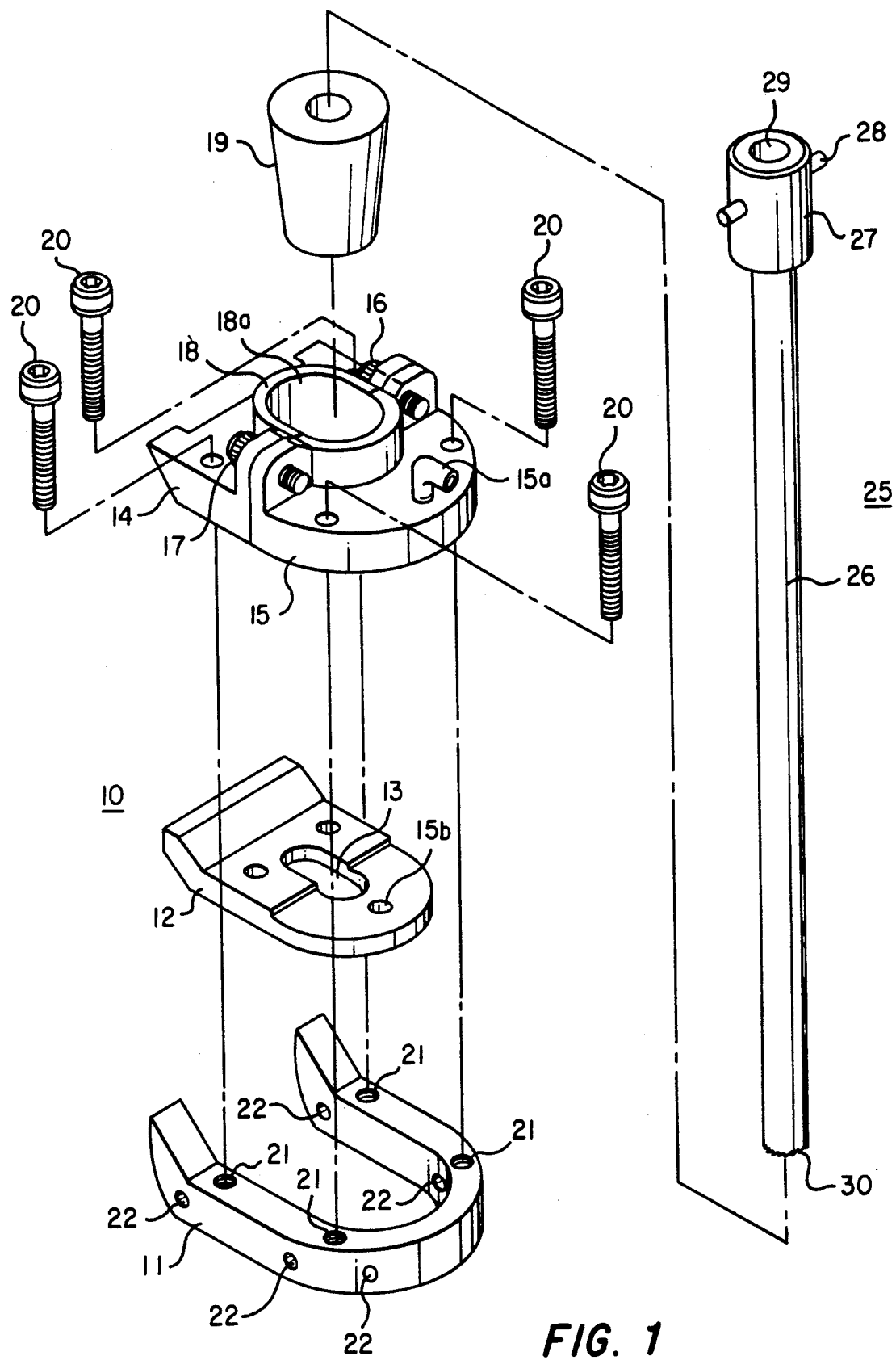
FIG. 1 illustrates a cylindrical bone cutter for simultaneous use with suction.

FIG. 1 illustrates a device which is similar to a prosthesis holder described in U.S. Pat. No. 5,047,061. In that patent the holder positions and holds a prosthesis in a femur during surgery. The present invention modifies the holder as shown by holder 10 in FIG. 1. In the present invention, the holder guides and positions a cutter used to remove medullary bone from the medullary canal in order to provide a sufficiently large canal to receive the femur prothesis. Holder assembly 10 also seals the medullary canal from the outside atmosphere.

Holder assembly 10 includes a base guide 11 that is attached to the upper femur bone 35 (FIG. 2) that has been modified by removing part of the upper femur bone such that a flat surface 36 is presented to the base guide 11. Base guide 11 is attached to the upper femur bone by pins 22a inserted in openings 22 in base guide 11, and into the femur bone 35.

Attached to base guide 11 is ceiling a plate which has two plates 14 and 15, and a collar 18. Plates 14 and 15 are bolted together by bolts 16 and 17, and then secured to base guide 11 by four bolts 20, which screw into threaded holes 21. Ceiling plate 14,15 has a collar 18 surrounding opening 18a, into which is placed cylindrical plug 19. Cylindrical plug 19 is held firmly in place by collar 18. Cutter 25 extends through cylindrical plug 19 and is used to remove part of the medullary bone to enlarge a portion of the medullary canal, as hereinafter explained. Shaft 26 of cutter 25 inside of cylindrical plug provides a seal, preventing air from entering the medullary canal.

An inlet 15a is in the top of plate 15. Inlet-15a is used to attach a pressure gauge to monitor negative pressure within the medullary canal. The negative pressure resulting from the suction, as hereinafter explained, is not to be too great so as to produce excess bleeding, resulting from the negative pressure in the canal. Inlet 15a may also be used for injecting irrigating fluid into the medullary canal. Opening 15b in gasket 12, directly below inlet 15a allows the flow of the fluid into the canal area.

Positioned between base guide 11 and ceiling plate 14, 15 is gasket 12. Gasket 12 serves as a gasket to provide a seal between the mating surfaces of base guide 11 and ceiling plate 14,15. Opening 13 allows the cutter shaft to pass through plate 12. The oval shape of opening 13 allows for tilting or moving cutter 25 to align with the medullary canal for removing bone axially with the canal.

Figure 2:
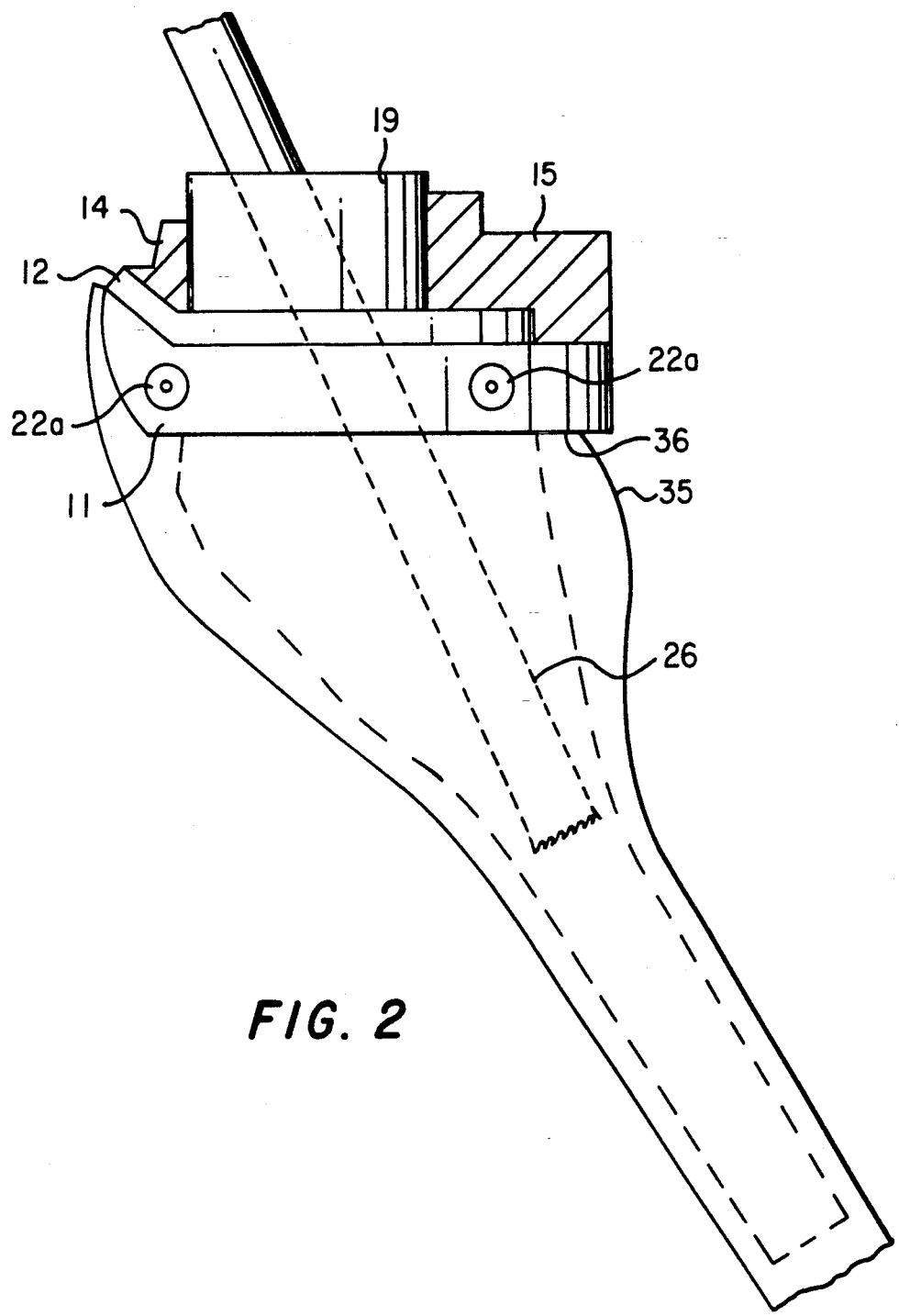
FIG. 2 illustrates the bone cutter guide of FIG. 1 mounted on a femur bone.

FIG. 2 shows holder assembly 10 mounted on the end of femur bone 35. Base guide 11 is attached to femur 35 on flat surface 36 by pins 22a. Plates 14 and 15, attached to base plate 11 holds cylindrical plug 19 through which cutter shaft 26 extends. Cylindrical plug 19 has an opening therein extending though cylindrical plug 19 at an angle to align cutter shaft 26 with the medullary canal. Various cylindrical plugs are used to accommodate cutters of different diameters, and to allow for different cutting angles.

Figure 3:
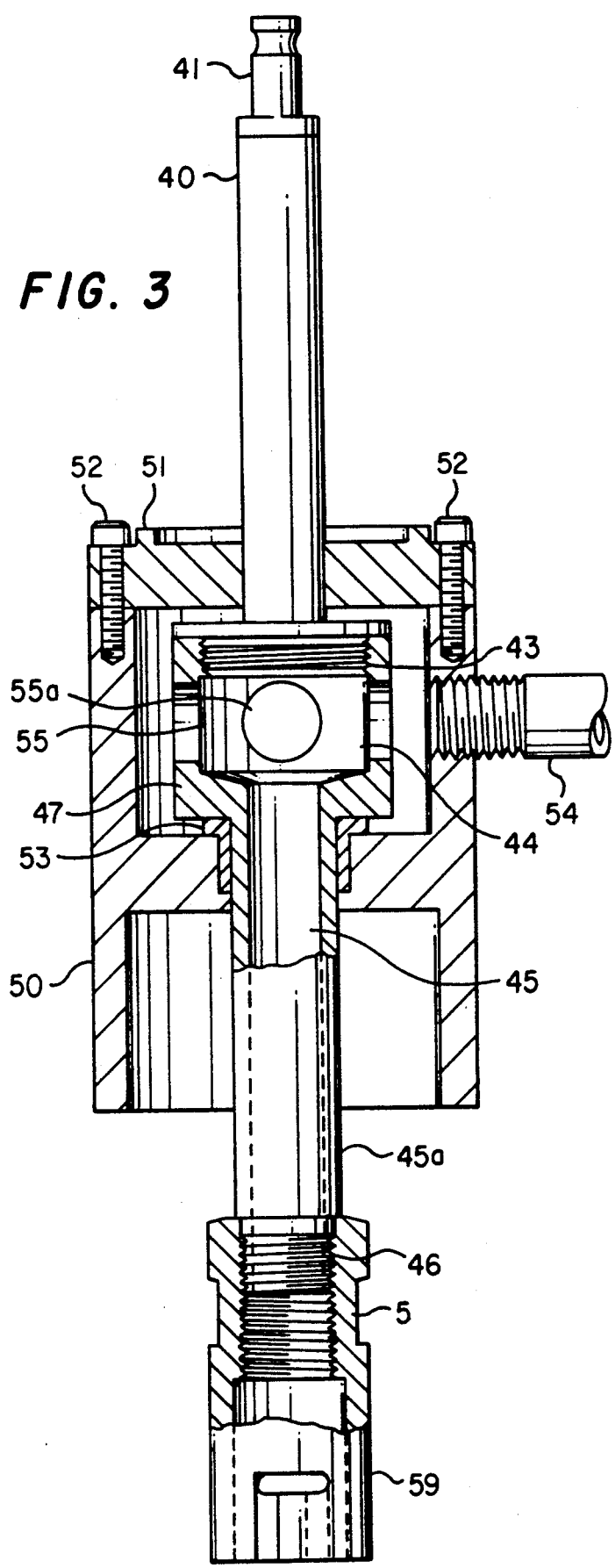
FIG. 3 illustrates a suction head and bone cutter guide with the cutter chuck.

FIG. 3 illustrates a drum housing 50 for providing a vacuum suction chamber to remove bone chips while cutting and enlarging the medullary canal, and to provide a coupling from the rotary power source to the cutter. Housing 50 includes a top 51 secured to housing 50 by screws 52. Extending through top 51 is drive shaft 40 which is attached to a rotary power source at end 41, and is attached to coupling 47 by threads 43. Coupling 47 is an internal coupling in housing 50 and has an upper section 55 having openings 55a through which a vacuum suction is drawn to remove bone particles. A suction line is attached to housing 50 by suction line 54. Bone fragments are suctioned from the cutting area through the cutter and coupler 47 through channel 45 The bone fragments drawing through channel 45 exit coupler 47 through openings 55a and out suction line 54.

Coupling 47 extends through cylindrical plug 53 which provides a seal between the bottom of housing 50 and the end 45a of coupling 47, which extends out the bottom of housing 50. Coupling 47 has a threaded end 46 which screws into internal threads 58 in cutter chuck 59.

Figure 4:
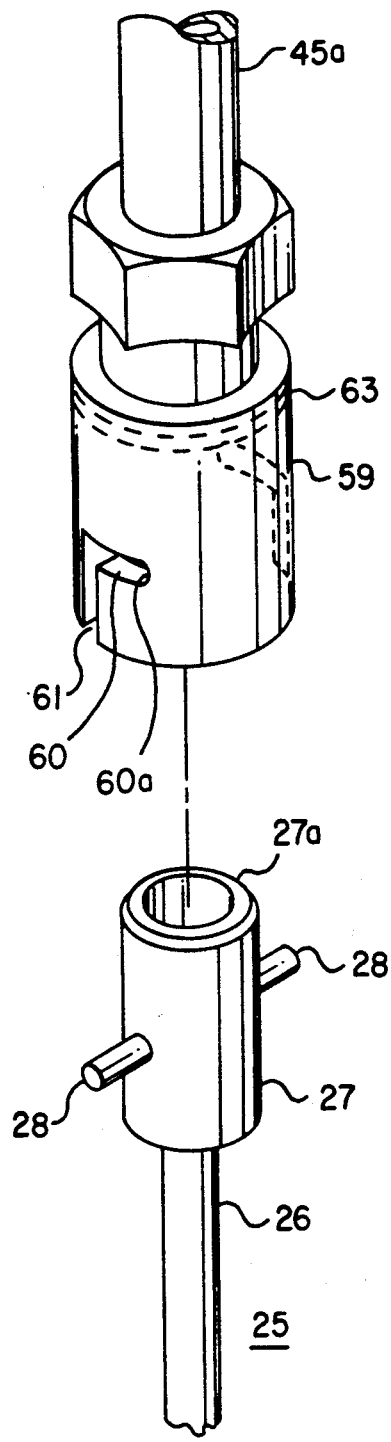
FIG. 4 illustrates the cutter chuck and cutter releases/hold mechanism.

FIG. 4 shows cutter chuck 59 in detail, and its interconnection with cutter 25. Chuck 59 is attached to coupling shaft 45 by screw threads as illustrated in FIG. 3, and attached to cutter 25 by a twist lock connector. Chuck 50 has two diagonally placed vertical channels 61 connected to horizontal channels 60. Cutter 25 has an enlarged tubular shank section 27 having a pair of pins 28 extending out opposite sides of section 27. Pins 28 are placed in vertical openings 61 as cutter 25 is mounted in chuck 59. Cutter 25 is moved up into chuck 59 until pins abuts against the intersection of channel 61 and channel 60. Cutter 25 is then twisted to move pins 28 into a locked position at end 60a of channel 60. Clockwise rotation of cutter 25 using cutting procedures holds cutter locked into chuck 59.

To provide a seal for the suction path through cutter 25 and chuck 59, O-ring 63 seals against the top rim 27a of tubular section 27 when cutter 25 is mounted in chuck 59. O-ring 63 is easily removed and replaced for cleaning FIGS. 5 and 5a illustrate a cutter and the cutting teeth. Cutter 25 has a tubular shaft 26 attached to a shank portion 27. Shaft 26 is hollow and channel 26a extends from the cutting teeth to shank 27. Shank 27 is also hollow and has central opening 27b which is an extension of channel 26a. Pins 28 are used to secure cutter 25 in chuck holder 59, as illustrated in FIG. 4. FIG. 5a is a partial view of the cutter shaft, shown in section, showing a transverse bar 70 extending across channel 26a. The lower edge of bar 70 is sharpened to break up large bone fragments from the bone drilling created by teeth 71. Teeth 71 are beveled or flared inward on cutting shaft 26 rather than on the outside which prevents little or no means for the small bits of cutting debris to escape to the intertrabecular spaces. The teeth end of each cutter is slightly flared to provide a large enough opening in the medullary canal for the cutter to clear the enlarged canal as the cutter is moved downward into the canal.

The removal of debris through the cutter internal channel 26a prevents the escape of debris which currently occurs with peripheral grooves found on reamers.

FIG. 6 shows a larger cutter 66 that is used after a first cutter 25 is used to remove bone higher up in the medullary canal. Since the medullary canal increases in size at its upper end, successively larger cutters must be used. Cutter 67 has a hollow cutting shaft 66 with shank 68 and mounting pins 67.

Figure 7:
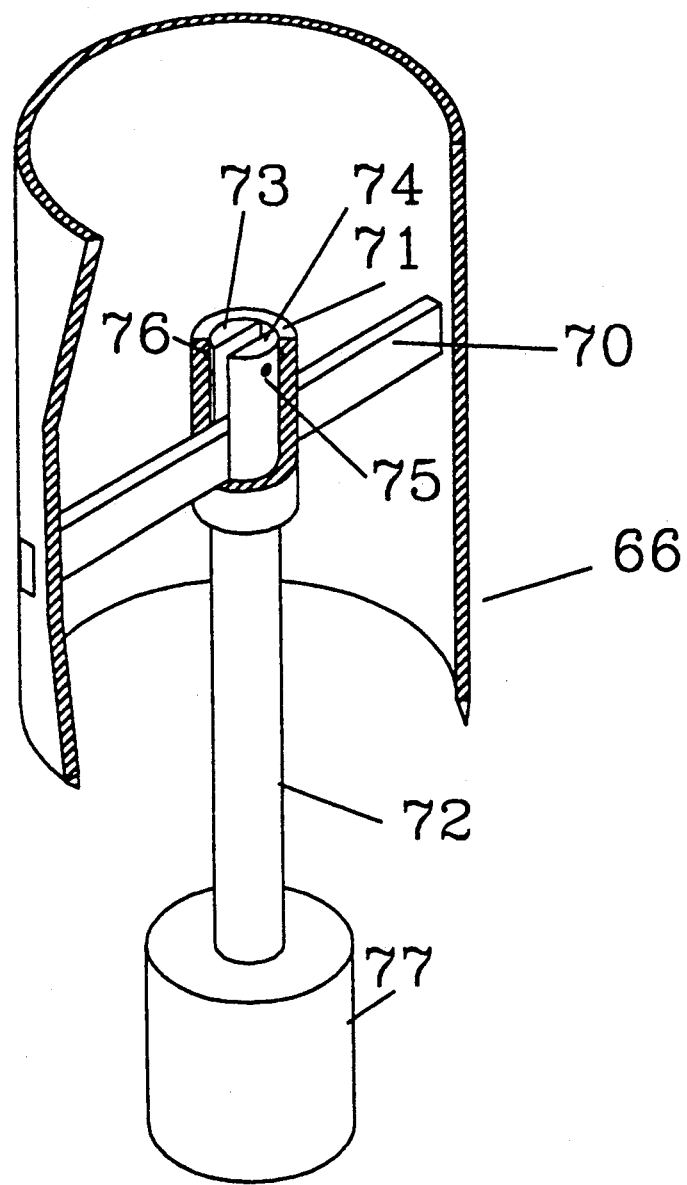
FIG. 7 illustrates a guide attachable within a cutter tip for positioning the cutter on subsequent cuts.

FIG. 7 illustrates a cutter guide attachable to the end of a cutter. After the first cutter has cut the initial cut in the medullary canal, a guide may be attached to subsequent cutters, the guide being the same size as the previous cutter. The guide aids in centering the subsequent cutters in the medullary canal. Guide 77 is attached to shaft 72 that is mounted in retaining cylinder 71. Shaft 72 has a split end 73,74 that is positioned about cutting bar 70. Inside cylinder 71 is a groove 76 that is used in conjunction with ball 75 to hold shaft 72 inside cylinder 71. As shaft 72 is moved into cylinder 71, ball 75 will snap into groove 76. The split end of shaft 72 provides a spring action that holds ball 75 in groove 76. A downward pull on shaft 72 will cause shaft ends 73,74 to flex inwardly allowing ball 72 to be pulled out of groove 76 and shaft 72 out of cylinder 71. Since different sizes of guides 77 are needed after each successive cut, the guide is easily removed and a different guide mounted in cylinder 71. The length of cylinder 71 and cutter 70 prevents the shaft and guide from turning and tilting during cutting operations.

With references to FIGS. 1–7, the cutting procedure is as follows. A guide base and ceiling collar (holder assembly) is mounted onto the flattened top of the femur bone (FIG. 1). A cutter is placed through the holder assembly at an angle placing the cutter co-axially aligned with the medullary canal (FIG. 2). The top or shank portion of the cutter is attached to a chuck by a twist-lock arrangement(FIG. 4). The chuck is attached to a coupling that extends into a housing to which a suction is applied. The coupling shaft is attached to a shaft connected to a rotary power source used for turning the cutter during the cutting/bone removal procedure. Suction is applied to an outlet connection in the suction housing such that when the cutter is removing bone within the medullary canal, bone fragments, fat and other debris is drawing up through the cutter shaft, into the suction housing, and out though the outlet to a collection container. Since the cutting teeth are beveled inward, bone fragments and other debris is directed to the inside of the cutter shaft channel, where it is removed by the suction applied to the suction housing.

Since the medullary bone canal decreases in diameter from the proximal end to the distal end, it is necessary to provide cutters with a relative wide range of transverse diameters. The surgeon first uses a small diameter cutter and removes the central portion of the medullary canal to the depth that is to be filled with cement, for holding the prosthetic stem. The depth is several inches longer than the prosthetic stem. Subsequent cutters of increasing size are used to increase the opening in the medullary canal, but each length of cut is shorter than the previous cut The removable guide at the end of a cutter provides for proper alignment of each subsequent cut.

What is claimed is:

1. An apparatus for enlarging the medullary canal prior to the insertion of a prosthetic device, comprising:
   a guide assembly for mounting on a femur, including a base plate adapted to be secured to the femur and a ceiling plate attached to said base plate;
   a gasket mounted between said base plate and said ceiling plate to form a seal therebetween;
   a bone cutter extending through the guide assembly;
   a suction housing attached to said bone cutter;
   a coupling shaft in said suction housing attached to said bone cutter allowing said cutter to rotate during bone removal; and
   a cylindrical plug through which said bone cutter extends.

2. The apparatus according to claim 1, wherein said cylindrical plug has an opening therein through which the bone cutter extends at an angle co-axial with the medullary canal.

3. The apparatus according to claim 1, wherein said cutter and coupling shaft are hollow, through which a suction is drawn from said suction housing to remove bone cutting and debris created during cutting operations.

4. The apparatus according to claim 1, wherein said cutter has a hollow shaft, and has a cutter bar mounted diametrically across the hollow shaft to break up bone fragments drawn through the cutter shaft 5. The apparatus according to claim 4, wherein said cutter has teeth on the cutting end that are beveled inward toward the center of the cutter shaft 6. The apparatus according to claim 1, wherein said suction housing includes a drive shaft attached to said coupling shaft for coupling a rotary power source to said coupling shaft and said cutter.

7. The apparatus according to claim 1, wherein said suction housing includes a suction outlet for attaching said housing to a suction/vacuum source, and includes a chamber for collecting bone fragments and other debris resulting from enlarging the medullary canal with said bone cutter.

8. An apparatus driven by a rotary power source for enlarging the medullary canal within a femur bone prior to the insertion of a prosthetic device, comprising:
   a guide assembly including an angled cylindrical plug for mounting on the femur, a base plate adapted to be secured to the femur, a ceiling plate attached to said base plate for mounting said cylindrical plug and a gasket mounted between said base plate and said ceiling plate to form a seal therebetween;
   a tubular bone cutter extending through the cylindrical plug in said guide assembly;
   a guide assembly for centering said tubular bone cutter in the medullary canal;
   a suction housing; and
   a coupling shaft mounted in said suction housing, turned by said rotary power source, said coupling housing attached to said bone cutter with a chuck for rotating said cutter during bone removal.

9. The apparatus according to claim 8, wherein said cylindrical plug has an opening therein through which the bone cutter extends at an angle co-axial with the medullary canal.

10. The apparatus according to claim 8, wherein said cutter and coupling shaft are hollow, through which a suction is drawn from said suction housing to remove bone cutting and debris created during cutting operations.

11. The apparatus according to claim 8, wherein said cutter has a hollow shaft, and has a cutter bar mounted diametrically across the hollow shaft to break up bone fragments drawn through the cutter shaft, and a guide to center the cutter.

12. The apparatus according to claim 11, wherein said cutter has teeth on the cutting end that are beveled inward toward the center of the cutter shaft.

13. The apparatus according to claim 8, wherein said suction housing includes a drive shaft attached to said coupling shaft for coupling a rotary power source to said coupling shaft and said cutter.

14. The apparatus according to claim 8, wherein said suction housing includes a suction outlet for attaching said housing to a suction/vacuum source, and includes a chamber for collecting bone and other debris resulting from enlarging the medullary canal with said bone cutter.

15. The apparatus according to claim 8, wherein said cutter has a mounting shank with twist-lock pins for mounting in the chuck on said coupling.

16. The apparatus according to any one of claims 8, 9, 10, 11, 12, 13, 14 and 15 wherein said ceiling plate is a two part plate which may be separated to insert an extender plate to accommodate different size femur bones.

17. A method for enlarging the medullary canal in a femur bone prior to the insertion of a prosthetic device, comprising the steps of:
   attaching a guide/sealing plate to a femur bone;
   inserting a hollow bone cutter through said guide/sealing plate; and
   applying a suction to said hollow bone cutter during cutting to remove bone fragments and other debris resulting from bone cutting.

18. The method according to claim 17, including the steps of cutting with increasingly larger size cutters to enlarge the medullary canal to accept a tapered stem prosthetic device.

19. The method according to claim 17, including the step of:
   aligning the cutter with the medullary canal prior to cutting.

20. The method according to claim 17, including the step of monitoring negative pressure with the medullary canal to prevent excess bleeding resulting form too great a negative pressure.

* * * * *